US008869617B2

(12) United States Patent
Arnau Vives et al.

(10) Patent No.: US 8,869,617 B2
(45) Date of Patent: Oct. 28, 2014

(54) METHOD AND DEVICE FOR NANOGRAVIMETRY IN FLUID MEDIA USING PIEZOELECTRIC RESONATORS

(75) Inventors: Antonio Arnau Vives, Valencia (ES); Pablo García Mollá, Valencia (ES); José Vicente García Narbon, Valencia (ES); Yolanda Jiménez Jiménez, Valencia (ES); Yeison Montagut Ferizzola, Valencia (ES); Antonio Reig Fabado, Valencia (ES)

(73) Assignee: Universidad Politecnica de Valencia, Valencia (ES)

( * ) Notice: Subject to any disclaimer, the term of this patent is extended or adjusted under 35 U.S.C. 154(b) by 375 days.

(21) Appl. No.: 13/336,082

(22) Filed: Dec. 23, 2011

(65) Prior Publication Data

US 2012/0152003 A1    Jun. 21, 2012

Related U.S. Application Data

(63) Continuation of application No. PCT/ES2010/070409, filed on Jun. 18, 2010.

(30) Foreign Application Priority Data

Jun. 23, 2009 (ES) .................................. 200901503

(51) Int. Cl.
*G01N 29/036* (2006.01)
*G01N 29/30* (2006.01)
*G01N 5/02* (2006.01)
*G01G 3/16* (2006.01)
*G01N 29/44* (2006.01)
*G01N 29/22* (2006.01)

(52) U.S. Cl.
CPC .................. *G01G 3/16* (2013.01); *G01N 29/30* (2013.01); *G01N 29/036* (2013.01); *G01N 2291/0255* (2013.01); *G01N 5/02* (2013.01); *G01N 29/4463* (2013.01); *G01N 2291/0256* (2013.01); *G01N 29/222* (2013.01)
USPC .............................................. 73/579; 73/580

(58) Field of Classification Search
USPC ............. 73/579, 24.03, 24.06, 28.01, 863.22, 73/865.5, 865.8, 61.49, 580
See application file for complete search history.

(56) References Cited

U.S. PATENT DOCUMENTS 4,817,430 A * 4/1989 Benes et al. .................... 73/579
5,201,215 A * 4/1993 Granstaff et al. ............ 73/54.41

(Continued)

FOREIGN PATENT DOCUMENTS

| ES | 2 153 740 | 3/2001 |
| ES | 1 607 725 | 12/2005 |
| WO | 2009/060100 | 5/2009 |

OTHER PUBLICATIONS

International Search Report issued Oct. 8, 2010 in International (PCT) Application No. PCT/ES2010/070409.

*Primary Examiner* — J M Saint Surin
(74) *Attorney, Agent, or Firm* — Wenderoth, Lind & Ponack, LLP.

(57) ABSTRACT

The invention relates to a method, to a device for electronic characterization, and to a measurement cell and support for monitoring a chemical or physical process with results that can be assessed in terms of the weight variation of a coating deposited on a piezoelectric sensor, exposed to a fluid medium with stable physical properties. The invention uses the deduction of an analytic expression establishing a simple connection between the phase variation of a fixed-frequency signal, which queries the piezoelectric resonator, and the variation in the bulk density of the coating. The invention is suitable for implementations that use piezoelectric resonators for characterizing biochemical and electrochemical processes, such as, inter alia: piezoelectric biosensors and immunosensors, process and material characterization by AC electrogravimetry, detection of dissolved chemical or biological substances.

10 Claims, 5 Drawing Sheets

(56) References Cited

U.S. PATENT DOCUMENTS

| | | | |
|---|---|---|---|
| 5,852,229 A * | 12/1998 | Josse et al. | 73/24.06 |
| 6,439,765 B2 * | 8/2002 | Smith | 374/31 |
| 6,510,727 B2 * | 1/2003 | Reiter et al. | 73/24.03 |
| 6,626,025 B2 * | 9/2003 | Potyrailo et al. | 73/7 |
| 6,942,782 B2 * | 9/2005 | Shevchenko et al. | 205/793.5 |
| 2004/0150296 A1 | 8/2004 | Park et al. | |

\* cited by examiner

METHOD AND DEVICE FOR NANOGRAVIMETRY IN FLUID MEDIA USING PIEZOELECTRIC RESONATORS

This application is a continuation of international application PCT/ES2010/070409, filed Jun. 18, 2010, which is hereby incorporated by reference in its entirety.

OBJECT OF THE INVENTION

The present invention relates to the field of chemical sensors, particularly to those using electrical measurements to detect extremely small changes of weight, and more particularly to those using piezoelectric resonators such as micro- or nano-balances in liquid media.

BACKGROUND OF THE INVENTION

Micro-scale sensors, and among them those based on piezoelectric quartz crystals, are devices used to accurately measure variations in the weight deposited thereon per unit area, through the changes withstood by the resonance frequency of such crystals operating as resonators. Among the variety of microbalance sensors currently existing on the market, the so-called AT cut quartz resonators (wherein this type of cut corresponds to a cut at an angle with an inclination of 35°15' with respect to the optical axis z of the crystal and perpendicular to the plane y-z thereof) are becoming an alternative analytical tool in a wide range of implementations, in which one wishes to detect the presence of species in solution or to characterize chemical processes, with a resolution comparable, in many cases, to the classical chemical techniques (See references: A. W. Czanderna and C. Lu (1984) in "Applications of piezoelectric quartz crystal microbalances", C. LU and A. W. Czanderna (eds), Elsevier, Amsterdam, Vol. 7; A. Janshoff, H-J Galla and C. Steinem (2000) "Piezoelectric mass-sensing devices as biosensors—an alternative to optical biosensors?" Angew. Chem Int. Ed. 39:4004-4032; MA. Cooper and V T. Singleton (2007) "A survey of the 2001 to 2005 quartz crystal microbalance biosensor literature: applications of acoustic physics to the analysis of biomolecular interactions" Journal of Molecular Recognition 20 (3): 154-184; T A. Carnesano, Y T. Liu and M. Datta (2007) "Measuring bacterial adhesion at environmental interfaces with single-cell and single-molecule techniques" Advances in Water Resources 30 (6-7):1470-1491; 0. Lazcka, F J. Del Campo and F X, Muñoz (2007) "Pathogen detection: A perspective of traditional methods and biosensors" Biosensors & Bioelectronics 22 (7):1205-1217; TS. Hug (2003) "Biophysical methods for monitoring cell-substrate interactions in drug discovery" Assay and Drug Development Technologies 1 (3): 479-488; FL. Dickert, P. Lieberzeit and O. Hayden (2003) "Sensor strategies for micro-organism detection—from physical principles to imprinting procedures" Analytical and Bioanalytical Chemistry 377 (3):540-549; K A. Marx (2003) "Quartz crystal microbalance: A useful tool for studying thin polymer films and complex biomolecular systems at the solution-surface interface" Biomacromolecules 4 (5): 1099-1120; K A. Fahnrich, M. Pravda and G G. Guilbault (2002) "Immunochemical detection of polycyclic aromatic hydrocarbons (PAHs)" Analytical Letters 35 (8): 1269-1300; J. Wegener, A Janshoff and C. Steinem (2001) "The quartz crystal microbalance as a novel means to study cell-substrate interactions in situ" Cell Bio-chemistry and Biophysics 34 (1):121-151; C K. O'Sullivan and G G. Guilbault "Commercial quartz crystal microbalances—theory and applications" Biosensors & Bioelectronics 14 (8-9):663-670; C K. O'Sullivan, R. Vaughan and G G. Guilbault (1999) "Piezoelectric immunosensors—theory and applications" Analytical Letters 32 (12):2353-2377; K. Bizet, C. Grabielli and H. Perrot (1999) "Biosensors based on piezoelectric transducers" Analysis EurJAC 27:609-616).

The use of the AT cut quartz crystal resonator as quartz crystal microbalance, better known by its initials in Anglo-Saxon literature as QCM (quartz crystal microbalance), is based on the well known, Sauerbrey equation (G. Sauerbrey (1959) "Verwendung von schwingquarzen zur wägung dünner Schichten and zur mikrowägung" Zeitschrift Fuer Physik 155 (2): 206-222), by those skilled in the art. Sauerbrey's equation states that the decrease in the resonance frequency of the resonator is proportional to the increase in the surface density in weight of the coating on the surface of the sensor. When the sensor is in contact with a Newtonian liquid medium, Kanazawa's equation (K.K. Kanazawa and J. G. Gordon II (1985) "The oscillation frequency of a quartz resonator in contact with a liquid" Analytica Chimica Acta 175: 99-105) provides the shift in the resonance frequency of the resonator due to contact with the fluid. For a QCM sensor with one of the surfaces coated with a very fine layer of material, so thin that the lag in the acoustic wave through the coating thickness is very small, and exposed to Newtonian liquid. Martin's equation (I) provides the quantitative connection of the combination of the effects of the coating weight (Sauerbrey effect) and the liquid (Kanazawa effect) in the variation of the resonance frequency (S. J. Martin, V. E. Granstaff and G. C. Frye (1991) "Characterization of quartz crystal microbalance with simultaneous mass and liquid loading" Anal. Chem. 63:2272-2281).

$$\Delta f = -\frac{2f_s^2}{Z_{cq}}\left(\rho_c h_c + \frac{1}{2}\rho_L \delta_L\right) \quad (I)$$

In the above equation, the first term of the second member corresponds to the Sauerbrey effect and the second one to the Kanazawa effect, wherein $f_s$ is the resonance frequency of the sensor, $Z_{cq}$ is the characteristic acoustic impedance of the quartz, $\rho_c$ and $h_c$ are, respectively, the density and thickness of the coating; and $\rho_L$ and $\delta_L$ are, respectively, the density and the depth of penetration of the acoustic wave in the liquid: $\frac{1}{2}\rho_L\delta_L$ is, in fact, the surface density of equivalent weight associated with the oscillating movement of the surface of the sensor in contact with the liquid medium.

According to equation (I), for a certain surface weight density of the coating, the absolute value of the frequency offset increases in direct proportion to the square of the resonance frequency. Consequently, it seems logical to think that a much greater sensitivity will have a QCM sensor the higher its resonance frequency is. In fact, the resonance frequency has always been the fundamental characterization parameter in QCM sensors.

Indeed, in practice, the vast majority of techniques used in the characterization of QCM sensors have been used to determine the variation in the resonance frequency of the resonator, and other relevant parameters thereof (the U.S. Pat. No. 5,201,215 granted to Granstaff et al. "Method for simultaneous measurement of mass loading and fluid property changes using a quartz crystal microbalance", includes other parameters of the sensor that should be monitored; see also references: A. Arnau, V. Ferrari, D. Soares, H. Perrot, "Interface Electronic Systems for AT-cut QCM Sensors. A comprehensive review", in *Piezoelectric Transducers and Applications*, 2nd Ed., pp. 117, A. Arnau Ed., Springer-Verlag Berlin Heidelberg, (2008); F. Eichelbaum, R. Borngräber, J. Schröder, R. Lucklum, and P. Hauptmann (1999) "Interface circuits for quartz crystal microbalance sensors," *Rev. Sci Instrum.* 70:2537-2545): network or impedance analyzers are used to determine the conductance of the resonator in the range of resonance frequencies and determine the frequency that corresponds with the maximum conductance (J. Schröder, R. Borngräber, R. Lucklum and P. Hauptmann (2001) "Network analysis based interface electronics for quartz crystal microbalance" *Review Scientific Instruments* 72 (6):2750-2755; S. Doerner, T. Schneider, J. Schröder and P. Hauptmann (2003) "Universal impedance spectrum analyzer for sensor applications" in Proceedings of IEEE Sensors 1, pp. 596-594); the art of decay, which is contained in U.S. Pat. No. 6,006,589 granted to Rodahl et al., in 1999 (see also reference M. Rodahl and B. Kasemo (1996) "A simple setup to simultaneously measure the resonant frequency and the absolute dissipation factor of a quartz crystal microbalance" *Rev. Sci Instrum.* 67:3238-3241), processes the resulting signal by disconnecting the signal with which the resonator has been excited for a certain time, at a frequency close to that of the resonance. This analysis ultimately provides information on the variation of the resonance frequency, series or parallel depending on the configuration, and the losses in the resonator; in the techniques based on oscillators the resonant sensor is used as an element for controlling the frequency of oscillation, allowing a continuous monitoring of a frequency that corresponds to a specific phase of the resonator in the resonance range. This frequency can be used in many applications such as reference to the resonance frequency of the resonator (see the following references: H. Ehahoun, C. Gabrielli, M. Keddam, H. Perrot and P. Rousseau (2002) "Performances and limits of a parallel oscillator for electrochemical quartz crystal microbalances" *Anal Chem.* 74:1119-1127; C. Barnes (1992) "Some new concepts on factors influencing the operational frequency of liquid-immersed quartz microbalances" *Sensors and Actuators A-Physical* 30 (3): 197-202; K. O. Wessendorf (1993) "The lever oscillator for use in high resistance resonator applications" in Proceedings of the 1993 IEEE International Frequency Control Symposium, pp. 711-717; R. Borngräber, J. Schröder, R. Lucklum and P. Hauptmann (2002) "Is an oscillator-based measurement adequate in a liquid environment?" *IEEE Trans. Ultrason. Ferroelect. Freq. Contr.* 49 (9): 1254-1259; S. J. Martin, J. J. Spates, K. O. Wessendorf, T. W. Schneider and R. J. Huber (1997) "Resonator/oscillator response to liquid loading" *Anal. Chem.* 69:2050-2054). The techniques based on oscillators are the simplest and quickest for monitoring the frequency, but have operating disadvantages in liquid medium, wherein numerous applications of great interest taken place; for such reason large efforts have been made for designing oscillators suitable for these applications, which have resulted in different patents such as: U.S. Pat. No. 4,783,987 granted to Hager in 1988 titled "System for sustaining and monitoring the oscillation of piezoelectric elements exposed to energy-absortive media"; U.S. Pat. Nos. 4,788,466 and 6,848,299 B2 granted to Paul et al., in 1988 and 1995, "Piezoelectric sensor Q loss compensation" and "Quartz crystal microbalance with feedback loop for automatic gain control"; U.S. Pat. Nos. 5,416,448 and 6,169,459 granted to Wessendorf in 1995 and 2001 "Oscillator circuit for use with high loss Quartz resonator sensor" and "Active bridge oscillator"; finally there is a group of techniques that could be so-called "hooking techniques" (see the references A. Arnau, T. Sogorb, Y. Jiménez (2002) "Circuit for continuous motional series resonant frequency and motional resistance monitoring of quartz crystal resonators by parallel capacitance compensation" Rev. Sci. Instrum. 73 (7): 2724-2737; V. Ferrari, D. Marioli, and A. Taroni (2001) "Improving the accuracy and operating range of quartz microbalance sensors by purposely designed oscillator circuit" IEEE Trans. Instrum. Meas. 50:1 1 19-1 122; A. Arnau, J. V. García, Y. Jiménez, V. Ferrari and M. Ferrari (2007) "Improved Electronic Interfaces for Heavy Loaded at Cut Quartz Crystal Micro-scale Sensors" in Proceedings of Frequency Control Symposium Joint with the 21 st European Frequency and Time Forum. IEEE International, pp. 357-362; M. Ferrari, V. Ferrari, D. Marioli, A. Taroni, M. Suman and E. Dalcanale (2006) "In-liquid sensing of chemical compounds by QCM sensors coupled with high-accuracy ACC oscillator" IEEE Trans. Instrum. Meas. 55 (3):828-834; B. Jakoby, G. Art and J. Bastemeijer (2005) "A novel analog readout electronics for microacoustic thickness shear-mode sensors" IEEE Sensors Journal 5 (5):1106-1111; C. Riesch and B. Jakoby (2007) "Novel Readout Electronics for Thickness Shear-Mode Liquid Sensors Compensating for Spurious Conductivity and Capacitances" IEEE Sensors Journal 7 (3): 464-469) which can be considered as sophisticated oscillators, because these include a feedback loop, wherein the sensor exciting source can be considered external thereto and wherein the feedback condition of the loop can be accurately calibrated. These techniques allow accurately monitoring the dynamic series resonance frequency of the resonator and some of them have been protected by patents (MI2003A000514, granted to Ferrari et al, "Metodo e dispositivo per determinare la frequenza di risonanza di sensori piezoelettrici risonati" and patent ES2197796 granted to Arnau et al., in 2004 "Sistema de caracterización de sensores de cristal de cuarzo resonante en medios fluidos, y procedimiento de calibración y compensación de la capacidad del cristal de cuarzo".

Other recent patents using, in one way or another, some of the described techniques or variations thereof but with a common objet that is monitoring the resonance frequency of the sensor have been reviewed (those granted to J. P. Dilger et al., in 2000 and 2001, U.S. Pat. No. 6,161,420, "High frequency measuring circuit" and U.S. Pat. No. 6,222,366 B1 U.S. "High frequency measuring circuit with Inherent noise reduction for chemicals resonating sensors"; that granted to J. R. Vig in 2001, U.S. Pat. No. 6,247,354 B1, "Techniques for sensing the properties of fluids with resonators"; the patent granted to Chang et al., in 2003, U.S. Pat. No. 6,557,416 B2 "High resolution biosensor system"; the patent granted to Nozaki in 2006, U.S. Pat. No. 7,036,375 B2, "QCM sensor and QCM sensor device"; that granted to Dayagi et al., in 2007, U.S. Pat. No. 7,159,463 B2 "Sensitive and selective method and device for the detection of trace amounts of a substance"; that granted to Itoh et al., in 2007, U.S. Pat. No. 7,201,041 B2 "Analysis method using piezoelectric resonator"; that granted to Zeng et al., in 2008, U.S. Pat. No. 7,329,536 B2 "Piezoimmunosensor").

The main reason to perform the monitoring of the resonance frequency of the resonator and, therefore, its variation is the existence of a simple connection between this variation and the physical quantities of interest in a real application. In this case the variation in weight surface density on the surface of the sensor, which may be due to changes in the density of the coating or the properties of the liquid media, has been presented in equation (I). In many applications, for example, in piezoelectric biosensors, covering a wide range of process characterization (see reference M A. Cooper and V T. Singleton (2007) "A survey of the 2001 to 2005 quartz crystal microbalance biosensor literature: applications of acoustic physics to the analysis of biomolecular interactions" Journal of Molecular Recognition 20 (3):154-184), the displacements experienced by the resonance frequency of the sensor are usually very small, in the neighborhood of tens of hertz in megahertz, and are due to the increase in weight of the sensitive thin layer covering the resonator, wherein the liquid medium substantially maintains its fluid physical properties constant. Therefore, great efforts are being made to improve the sensitivity of the quartz crystal microbalance sensor; most of these efforts are aimed at increasing the resonance frequency of the resonator, as suggested by equation (I). However, equation (I) provides a theoretical ideal sensitivity that implicitly assumes an infinite stability of the components of the system for characterization and the measurement process, such that there are no disturbances associated with the measurement system or instabilities coming from the electronic system for characterization. Unfortunately this is not so, and the sensitivity does not exclusively depend on the resonator, but also on the design and configuration of the measurement system and the characterization electronic circuit. The entire infrastructure required for performing the experiment, including the measurement cell, flow elements, pumps, systems for adjusting the temperature, etc., except the characterization electronic circuit are understood here as the measurement system. Assuming that the measurement system has been designed to minimize disruptions and interferences that can affect the resonance frequency of the resonator such as: temperature changes, vibration, changes in the pressure of the fluid by the use of inadequate injection pumps, etc., the sensitivity of the assembly will depend on the accuracy of the measurement of the resonance frequency of the sensor which, in turn, will depend on the interference generated by the electronic system for characterization itself. Therefore, the sensitivity cannot be adequately assessed without considering the system used to characterize the sensor.

The systems used to characterize the piezoelectric resonators in microbalance applications, most of which have been described above, can be classified into two types: a) those that passively interrogate the sensor kept outside the characterization system, and b) those in which the sensor is part of the characterization system itself. The network or impedance analyzers and the techniques of decay are in the first group, whereas the second group may include the oscillators. The hooking techniques can be considered to be found between both groups.

The advantages of network or impedance analyzers are recognized and are associated with the fact that the sensor can be characterized after a calibration wherein any electrical influence external to the sensor itself has been balanced. Decay methods provide high accuracy, as long as the precision in the acquisition of the decay signal is high, both in phase and amplitude, resulting complex for high-frequency resonators. Thus, for high frequency resonators, higher than 50 MHz, only the impedance analyzers are accurate enough, but the high cost and size thereof make them unsuitable for implementations as sensors. Hooking techniques provide simpler circuits than the analyzers at relatively low frequencies of the resonators; but at high frequencies the circuit complexity increases and the advantages as for simplicity represented with respect to the analyzers or decay techniques are considerably reduced. Consequently, the oscillators become an alternative for monitoring the resonance frequency in high frequency resonators; the low cost, integration capability thereof and the rapid and continuous monitoring of the resonance frequency make them to the selected alternative to implement the QCM sensors at high resonance frequencies. However, in an oscillator, the sensitivity is determined by the stability of frequency and this by the stability of phase, which depends on the phase response of all the components of the oscillator system. In principle, the role of a resonator in an oscillator is to absorb the phase changes occurring in the other components of the oscillating system. The steep slope of the phase-frequency response of the resonator makes these phase changes compensated by with very small variations in the oscillation frequency. However, the variations experienced by the sensor are precisely of interest in the case of a QCM sensor, whereby any variation in the phase response of the other components forming the oscillator circuit will result in frequency instability. Moreover, the quality factor of the resonator as a sensor is greatly reduced in implementations in liquid medium, therefore relatively small changes in the phase response of the other components of the oscillator will result in relatively large variations in the oscillation frequency, which will appear as noise. The frequency and phase noise increase with the frequency of the system, therefore, it is not obvious to say that an increase in the resonance frequency of the sensor will necessarily imply an increase of the sensitivity of the sensor system, as shown in equation (I).

An alternative approach would be to interrogate the sensor with a test signal (so-called test signal) coming from an outside source of great stability in frequency and phase, similarly to what impedance or network analyzers do, but at a test frequency (or frequency test) set within the band of resonance of the sensor. A change in the phase-frequency response of the resonator, for example due to a variation in the weight surface density of the thin layer deposited on the resonator, would be detected from the phase change endured by the test signal. In principle, this phase change should be quantitatively related to the variation in weight on the surface of the sensor. U.S. Pat. No. 5,932,953 granted to Drees et al., claims a method and system based on this idea, which has the following advantages:

The stability of the test signal can be very high so that the precision in the characterization of the response of the sensor is not disturbed by the noise itself of the characterization signal.

The measurement of the lag is performed between the original signal, at the input of the circuit, and the resulting signal affected by the response of the sensor. Therefore, the measurement of lag is differential and any phase instability of the original test signal is simultaneously transferred to the output signal canceling each other out in the differential measurement.

The measurement of the lag can be accomplished with relatively simple circuitry, even at very high frequencies, therefore the system can be implemented by using a simple and easily integrated electronics.

When using a fixed-frequency test signal, the same signal, or a one synthesized therefrom, can be used to simultaneously interrogate other sensors, which greatly facilitates the implementation of systems with multiple resonators.

However, these apparent advantages that, in effect, could be provided by a measurement method and system based on the original idea of interrogating the sensor device with a fixed-frequency test signal, are never quite achieved by the method and system presented in U.S. Pat. No. 5,932,953 mentioned for the following reasons:

1.—The method claimed in said invention assumes that the measurement of phase provides a quantitative measure of the variation in weight of the sensitive coating deposited on the surface of the resonator; however it provides no mathematical connection between said phase variation and the corresponding weight variation. Therefore, in order to apply said method, a calibration of the sensor device would be necessary; which complicates the application of the claimed method. Moreover, in such patent, it is assumed that the sensitivity given by the connection between the variation of the phase insertion and the weight variation also increases in proportion to the frequency, in the same manner that the connection between the variation in the resonance frequency and the weight variation. This assumption is caused by lack of rigor in the analysis of the problem which intends to be satisfied with the method and system presented in this patent. As discussed in the detailed description of the present invention this is not the case, still more, for resonators in vacuum or gaseous medium, the sensitivity given by the connection between the variation of the insertion phase and the weight variation does not increase in vacuum, and do it slightly in a gaseous medium, by increasing the resonance frequency of the sensor, while in liquid medium it is proportional to the square root of the resonance frequency. This result shown for the first time in the present invention demonstrates that the object thereof is not a simple or trivial modification of the patent before.

2.—The method and system claimed in the U.S. Pat. No. 5,932,953 assume that the frequency of the test signal can be any frequency within the band of resonance of the sensor. As it will be demonstrated in the present invention, this is not true. The test signal which has to be used to establish the phase base or reference line must necessarily be, or be very close to, that so-called "dynamic series resonance frequency" of the sensor (such frequency known as DSRF and defined in the detailed description of the invention); in contrast the measures of the phase variation cannot simply relate to the weight variation, since this connection would depend on the exact frequency of the test signal and the sensor used, which would invalidate any calibration performed at a another frequency and make impractical the implementation of the claimed method. In this sense, the system claims, based on the simultaneous differential measurement of lags produced by two resonators resonance bands of which overlap, one of which is used as reference to cancel the external effects such as temperature, viscosity, etc., and in which the frequency of the test signal is set at the intermediate zone of the overlapping band, does not provide the desired results because the sensors are interrogated in different areas of their phase-frequency response; therefore external effects produce different responses in each resonator, which prevents their cancellation.

3.—Moreover, the selection of the frequency of the test signal, such as revealed in the previous section, has not been scheduled in the claimed method, or the claimed system. Accordingly, the claimed system is not suitable for appropriate measuring the phase variation at the convenient frequency. The system object of the present invention takes into account this aspect, resulting from a rigorous analysis of the problem and, therefore, it is not the result of a simple or trivial modification of the system shown in the patent cited above.

4.—The method and system claimed in the U.S. Pat. No. 5,932,953 only set the measurement of the phase variation. However, the exclusive measurement of the phase variation does not allow ensuring that the phase variations are exclusively related to weight variations in the sensor. Indeed, if the physical properties of the fluid medium on the resonator change, the phase variations can be disrupted by such change by inducing error in the characterization of weight variations. It is thus necessary to include in the system a way that allow establishing the validity of the connection between phase and weight variations.

5.—As mentioned, the phase-frequency sensitivity does not increase with the resonance frequency for the case of vacuum or gaseous medium, even for liquid media it does not increase as much as was expected; therefore it may still be desirable to use the measure of the resonant frequency variation as a characterization parameter. This aspect is not considered by the system claimed in the U.S. Pat. No. 5,932,953 since it has not been revealed until now. The system object of the present invention considers this aspect, after analyzing that the detailed description includes, implementing a feedback system that allows establishing both the appropriate test frequency and the optional measure of the resonance frequency variation.

6.—The U.S. Pat. No. 5,932,953 claims a method and a system wherein the sensor is interrogated with a fixed frequency signal within the band of resonance of the sensor. Once set the test frequency, it remains constant throughout the measurement process. The claimed method and system do not consider the shift suffered by the test frequency, within the resonance area during the measurement process, as a result of the displacement of the phase-frequency curve of the resonator. In addition, it does not provide any procedure for performing the selection of the appropriate test frequency within the resonance area of the sensor. This aspect is very important, as already indicated and as will become apparent in the detailed description of the invention below. the insertion of a controlled feedback that allows fixing the proper frequency of the test signal and, at the same time, determine how the frequency of the test signal is away from its optimum value during the experiment to be monitored, is a nontrivial improvement to the system and method claimed, already presented in the previous section. This aspect is particularly relevant since the modification of the phase-frequency response of the resonator during the experiment may lead to the test signal being eventually interrogating the sensor in a region of its phase-frequency response wherein there is no sensitivity, or this has been greatly reduced, i.e. wherein there is no phase variation exposed to variations in the coating weight; in another way, the response of the sensor is saturated. In particular, in gaseous medium, the saturation of the sensor may rapidly occur, i.e. the excursion of the response between the phase variation and the weight variation can be very short, since the frequency-phase response of the sensor is very abrupt. Therefore, including a method and a system allowing assessing the degree of deviation of the frequency of the test signal, with respect to its optimum value, during the measurement process, and allowing correcting said test frequency in an appropriate and automatic manner when the deviation of the test frequency is above a previously determined value is an important object of improvement.

7.—Finally, the system claimed in the U.S. Pat. No. 5,932,953 merely establishes the measurement of the phase variation of the sensor as a whole. As demonstrated in the detailed description of the present invention, it is necessary to design a system allowing measuring, as accurate as possible, the phase variation due to the change in the response of the mainly associated impedance to the dynamic branch of the sensor. An inadequate design of the system would reduce the sensitivity of the sensor system.

In addition to a suitable electronic characterization method and system, another difficulty to overcome when trying to work with resonators of mainly very high resonance frequency, is their small size and fragility; these features make it extremely difficult to design a measurement cell that meets the following specifications: the electrical contacts of the resonator for connection to the electronic characterization system must be extended and the isolation of one side of the resonator of the fluid medium without excessively disturbing the response of the sensor must be allowed, the conduction of experiments in flow, which a fluid is channeled so as to be in contact with at least one vibrating surface of a piezoelectric resonator has to be facilitated, and a safe handling of the sensor by the experimenters must be allowed. The invention aims to increase the sensitivity of current microbalance systems, whereby it presents both an electronic characterization method and system that must be accompanied by a suitable measurement cell that makes feasible both the application of the method and the electrical characterization of the resonant sensor. Currently there is no measurement cells prepared to work with AT-cut piezoelectric quartz resonators with mainly frequencies above 50 MHz for the reasons mentioned. The present invention provides a support and measurement cell that solves these problems.

The above analysis has served to highlight some key and differential features of the object of the present invention, which are not limited to the mentioned patents but are mostly general to currently existing systems.

BRIEF DESCRIPTION OF THE INVENTION

It is therefore a main object of the invention to provide a method, an electronic device and a measurement cell for characterizing a chemical or physical process outcome which can be assessed in terms of transfer, accumulation or loss of weight on a coating deposited on a piezoelectric sensor, and exposed to a fluid medium physical characteristics of which remain stable. The invention takes advantage of the deduction of an analytical expression establishing a simple connection between the phase variation of a fixed frequency signal, which interrogates the piezoelectric resonator, and the variation in the weight density of the coating deposited on the resonator. The present invention provides a substantial improvement and avoids the disadvantages of previous systems. Additionally, the proposed method is valid for any resonator operating in shear mode (said mode defined as that mode in which the particle displacement is parallel to the sensor surface and the wave propagates in the direction perpendicular to the displacement, that is it generates a transverse wave propagation) such as, for example, AT-cut quartz resonators or volume and thin film acoustic wave resonators, better known by its acronym in English FBAR (Film Bulk Acoustic Resonators), some of which can also vibrate in mode shear.

It is also an object of the present invention to provide a method and system that does not require the incorporation of sensor resonators in oscillator circuits.

It is an object of the present invention to provide a method and system that avoids the use of complex and expensive systems based on impedance analyzers or decay systems for measuring the transfer, accumulation or loss of weight that occurs over a coating deposited on a resonator piezoelectric, during a physical or chemical process, while providing an increase in the sensitivity.

Is a priority objective of the present invention to provide a method which uses a simple mathematical connection, to obtain a quantitative measure of the weight variation suffered by the coating deposited on at least one of the surfaces of the resonator sensor, from the phase variation experienced by a fixed and specific frequency signal, within the resonance region of the sensor, when transmitted through the resonant sensor during the physical or chemical process to be characterized, thus avoiding the performance of complex calibration procedures.

It is another main object of the invention to provide a method and system that allow establishing the optimal frequency of the test signal used to interrogate the resonant sensor, wherein the connection between the phase variation and the weight variation mentioned above is valid; and method of which considers and the system allows the correction of the frequency of the test signal in case of deviation therefrom, with respect to its optimal value, when moving the phase-frequency response of the resonator by the effect of the weight variation of the coating, is greater than a previously determined value; thus avoiding the saturation in the response of the resonant sensor.

It is still another object of the present invention to provide a method and system that allow selecting between monitoring the dynamic series resonance frequency or monitoring the phase variation of the test signal, as parameters for characterize the resonant sensor during the experiment.

It is an object of the present invention to provide a method and system allowing obtaining a measure of the phase variation withstood by a fixed frequency signal transmitted through the resonant sensor, mainly by effect of the variation of the phase-frequency response of the dynamic branch of the sensor, thus maximizing the connection between the phase and the weight variations.

It is still another object of the present invention to provide a system wherein the measurement of the phase variation is substantially free from factors external to the sensor coming from the environment.

It is still another object of the present invention to provide a support and measurement cell extending the electrical contacts of the resonator allowing its connection to the electronic system for characterization, that isolates one side of the resonator from the liquid medium in contact with the coating, which allows performing flow measurements and which provides a safe handling of the sensor by the experimenters, and all these without excessively disturbing the phase-frequency response of the sensor.

According to these and other objects of the invention there is provided a method for characterizing the transfer, accumulation or loss of weight of a coating deposited on a piezoelectric sensor, and exposed to a fluid medium physical characteristics of which remain stable, which includes the following operations:

1.—To apply a test voltage signal to a circuit wherein the resonant sensor is connected.

2.—To select the frequency of the test signal substantially equal (this term being understood as an equal or very close frequency) to the dynamic series resonance frequency of the resonator in the state being considered as reference.

3.—To measure the values of two voltage signals, one of which establishes the phase reference of the sensor and the other one the level reference of the losses thereof.

4.—To monitor the voltage values previously taken as a reference in the process to be characterized and monitored.

5.—To ensure that the value of the sensor loss reference voltage is not substantially modified during the experiment.

6.—To correct the frequency value of the test signal during the process to be monitored, in case that the signal providing the measurement of phase variation has deviated above or below a previously determined value, the value set as phase reference of the sensor in the above point 3, until the signal that provides the measurement of the phase variation has the same value as that set as phase reference of the sensor in the above point 3, or its difference in absolute value is less than some previously determined amount.

7.—To obtain the weight variation on the coating during the experimental process that has been monitored, from the variations of the signal that provides the measurement of the phase variation through the application of a simple analytical expression that connects the phase variation withstood by the test signal established in step 2, when passing through the circuit to which the sensor is connected, with the weight variation sought.

According to the previously stated objectives is provided an electronic system for characterizing the transfer, accumulation or loss of weight of a coating deposited on a piezoelectric sensor, and exposed to a fluid medium physical characteristics of which remain stable, which allows implementing the method described above and including:
- a source of certain fixed frequency, with high stability and low phase noise signal,
- a frequency synthesis subsystem;
- a signal control and acquisition subsystem;
- a signal conditioning circuit with filtering capability and adequacy of power levels;
- circuit formed by two branches that share the input and has two outputs, one for each branch. One branch is composed of components phase-frequency response of which does not change; the other one includes, in part, the same components as the first as a mirror, but a part of the components is replaced by the resonant sensor;
- Adjustable gain phase detection subsystem, which provides a voltage signal proportional to the phase difference between the signals at their inputs; and
- a power measurement subsystem that provides a voltage signal proportional to the difference between power levels of signals at their inputs;

and characterized in that:
- the frequency synthesis subsystem provides, from the fixed frequency signal, a signal frequency of which can sweep the band of resonance frequencies of the resonator sensor;
- the signal provided by frequency synthesis subsystem is connected to the input of the signal conditioning circuit that adequately filters it and provides the appropriate power level;
- the output of the signal conditioning circuit is connected to the input of the circuit of two branches wherein the resonant sensor is connected;
- each of the outputs of the circuit of two branches is connected to one input of the phase detection subsystem, output of which provides a continuous voltage signal with a value proportional to the phase difference between the signals at their inputs;
- Each one of the outputs of the two branches circuit is also connected to one input of the power measurement circuit, output of which provides a continuous voltage signal with a value proportional to the power levels difference between the signals at their inputs;
- the outputs of the phase detection circuitry and of the power level are acquired by the control system that can act on the frequency synthesis subsystem to control the frequency of the output signal from said subsystem;
- the data from the signals acquired by the control system are directly analyzed according to the method step 7 above mentioned, or either transferred to an external equipment for processing in real time or later in accordance to said method.

In accordance with the objectives previously mentioned a measurement cell and support for characterizing the transfer, accumulation or loss of weight of a coating deposited on a piezoelectric sensor, and exposed to a fluid medium physical characteristics of which remain stable, and which consists of:
- a support on which the resonant sensor is deposited and which extends the electrical contacts of the resonator while providing robustness and ease of use;
- a lower block which is deposited on the support, and which allows the connection of the electrical contacts extended from the resonator, through the support, to a conventional connector that provides the electrical connection of the resonant sensor to the characterization electrical system;
- an upper block, which includes the flow system and connection of which makes the support to be located between the two blocks, isolating one parts of the resonant sensor from the flow;

and characterized in that it extends the electrical contacts from the resonator allowing their connection to the electronic system for characterization described above, in that it isolates one face of the resonator from the liquid medium in contact with the coating, in that it allows performing flow measurements and in that it provides a safe handling of the sensor by the experimenters, without excessively disturbing the phase-frequency response from the sensor.

The objects and advantages of the present invention will become more apparent bellow from a detailed description of the invention.

DESCRIPTION OF THE DRAWINGS

To complement the description being made and in order to help better understand the features of the invention, according to a preferred embodiment thereof, is attached as an integral part of this description, a set of drawings in which in an illustrative and not limitative manner the following has been represented.

DETAILED DESCRIPTION OF THE INVENTION

Figure 1:
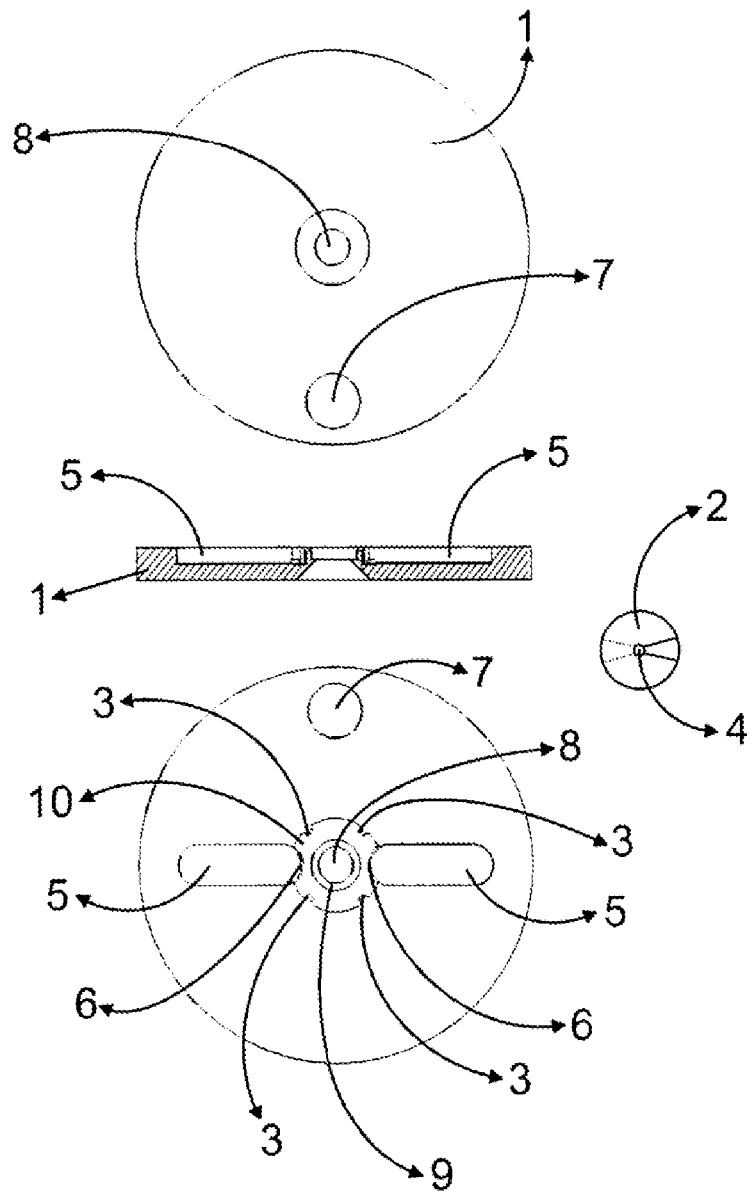
FIG. 1.—Represents the plant, lower floor, and cross section of the elevation of a support for depositing a piezoelectric sensor; it also shows the floor of a piezoelectric resonator.

FIG. 1 shows the plant, lower floor and a cross sectional of an elevation specially designed to accommodate a resonant sensor. The support aims to extend the resonator electrical contacts allowing their connection to an electronic system for characterization, and providing robustness and ease of operation of the sensor by the experimenters. The design of such support is that it provides such objectives without excessively disrupting the frequency-phase response of the sensor, and it is therefore a preferred embodiment of one of the priority objectives of the present invention.

In relation to the object of the invention presented in FIG. 1, on the support 1, made of a material with suitable features for supporting the contact with solid and liquid elements that have to be used in a particular experiment, there has been performed a machining consisting of the following elements: the protrusions 3, slots 5, ribs 6, holes 7 and 8 and midrib 9, leaving the gap 10 between the protrusions and nerves 6 and 9. By performing the mentioned support 1, a quartz resonator 2 is deposited between the protrusions 3 and over the ribs 6 and 9; the protrusions 3 serve as guides during the process for placing the resonator, such that the center of the resonator coincides with the center of the hole 8; in this position the ends of the electrodes of the resonator 4, properly protrude from the ribs 6 each reaching each one of the slots 5. The gap 10 under the resonator is filled, prior to the placement of the resonant sensor 2, with a sealing paste with suitable physical characteristics, being important that such paste does not shrink when dry. In this situation, the center of the electrode 4 located on the lower face of the quartz is accessible, through the hole 8, by the underside of the support 1. The ribs 6 and 9 act as a wall, so that the liquid paste fills the gap 10, as long as the properly amount is deposited, does not overflow over them. Once the resonant sensor has been deposited and sealed, the ends of the electrodes 4 are accessible from the slots 5; in this position a conductive liquid paste is placed in slots 5 establishing contact with the ends of the electrodes 4, the ribs 6 act as wall and avoid this paste from being spread over the surface of the glass outside the area of the slots 5. Once the conductive paste has been dried, the sensor electrodes 4 have been extended through the conductive paste along the length of each one of the slots 5. Once located and sealed the resonator as described above, the resonator is inserted into the support such that after the support is deposited for either side on a flat surface, the resonator does not touch such surface; in this way, the support provides the robustness necessary for a safe handling of the resonator, while allowing an extension of the electrical contacts of the same. The described design does not substantially alter either the response of the resonator. This support is used in conjunction with other elements of the measurement cell, the hole 7 is used to fix the position of the support in relation to the other element of the cell.

Figure 2:
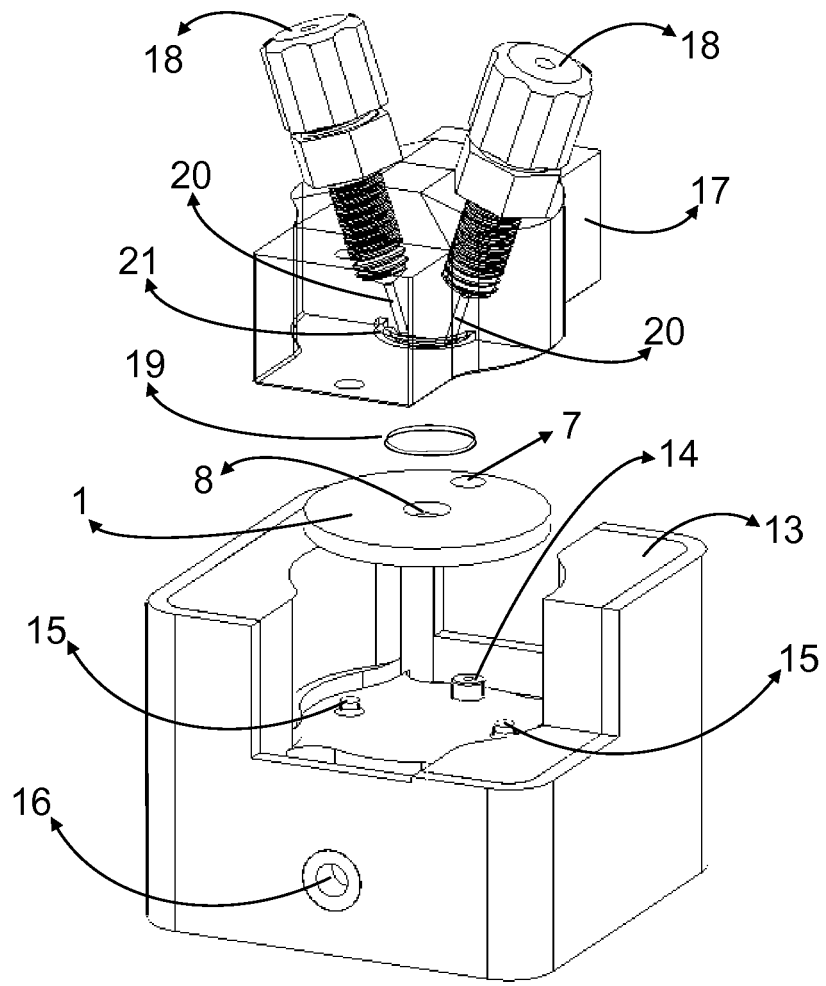
FIG. 2.—It is an exploded view of entire measurement cell object of the invention which have transparent parts of same for better visibility of certain details.

FIG. 2 shows a not limiting example of the use of the support in a measurement cell. In FIG. 2 the support is arranged between two blocks as a sandwich. The lower block 13 includes a protrusion 14 that allows fixing the position of the support 1 by fitting the protrusion 14 in the hole 7; the block 13 includes electrical contacts 15 inside of which there is included a spring so that the upper part of the electrical contact yields under certain pressure; the electrical contacts 15 are located so that they fit into the ends of the slots 5 when depositing the support with the slots 5 facing down, so that the electrodes of the resonator 4 are extended through the slots and the electrical contacts 15 to an external connector 16 that allows the connection of the resonator to an electronic system for characterization. In this arrangement the central area of one of the electrodes of the resonator is accessible from above through the hole 8 of the support. The upper block 17 is placed on the support and this is pressed by both the upper block 17 and the lower block 13, so that the washer 19 of suitable material, which fits into the slot 21 of the upper block, seals the boundary of the hole 8 of the support; the pressure between the blocks and the support can be adjusted by bolts, screws or other suitable system included in the upper and lower blocks, however, this pressure is not directly performed on the resonant sensor but on the support, thus avoiding substantially affecting the response of the sensor. In this arrangement, the channels 20 of the upper block 17 allow guiding a fluid, through fittings 18, which comes into contact with the central area of one of the electrodes 4 of the resonator 2; one of the fittings 18 is used as input and the other for outflow. The assembly shown in FIG. 2 shows one possible way to use a support 1, extending the electrical contacts of the resonant sensor and providing the robustness suitable for safe handling of the sensor by the experimenter, while isolating one of the electrodes of the resonant sensor from a fluid properly guided to get in contact, along its route, with the other electrode of the resonator, and all without disturbing the response of the sensor. Consequently, the shown example is not limited to implement one of the priority objectives of the present invention and can be considered a preferred embodiment thereof.

The above example has shown a support and measurement cell allowing designing an experiment in which a resonant sensor may be coated, by one of the faces, by a thin layer of material and this is in contact with a fluid medium. In the application scope of which the present invention is object, the coating on one side of the resonator is a weight layer thickness of which is thin enough as compared to the depth of penetration of the acoustic wave in the fluid medium in contact with the coating, is solid and is rigidly attached to the surface of the resonator using the proper technique; this ensures a synchronous motion with the oscillating surface of the resonator.

Figure 3:
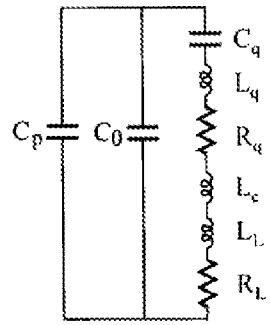
FIG. 3.—Represents an equivalent electrical model of a piezoelectric resonator.

A resonator in contact by one of its sides with an acoustically thin weight layer whereon there is a fluid medium long enough so as the acoustic wave generated in the resonator is attenuated in the medium before reaching its end, it can be electrically modeled by the equivalent circuit shown in FIG. 3. The equivalent circuit shown in FIG. 3 represents the electrical admittance of the resonator in contact with the coating and the fluid; the equivalent model parameters are related to physical and geometric properties of the resonator and the media deposited thereon. The equivalent circuit consists of the capacitance $C_0$, so-called static capacity, which corresponds to the capacitance formed by the quartz crystal as a dielectric between the electrodes, the capacitance $C_p$ that is the stray capacitance outside the sensor viewed between its electrodes, and the dynamic impedance comprising the circuit in series formed by $L_q$, $C_q$, $R_q$, $L_c$, $L_L$ and $R_L$. The parameters $L_q$, $C_q$, $R_q$ represent the dynamic contribution of the sensor in vacuum and only depend on geometrical and physical properties of the resonator, while $L_c$, $L_L$ and $R_L$ represent the contribution of the load on the resonator: $L_c$ models the contribution of the coating on the dynamic impedance and is proportional to the weight surface density of the coating $m_c = \rho_c h_c$, where $\rho_c$ is the density of the coating material and $h_c$ the thickness, that is $L_c = K_t m_c$, where $K_t$ is the constant of transformation that relates the physical properties and electrical parameters, and which is given by, wherein $h_q$ is the thickness of the resonator, $e_q$ is the piezoelectric stress coefficient of the interest vibration mode of the resonator during the implementation and $A_s$ is the area of the electrodes in the area where the electrodes of one and other side of the resonator are faced, i.e. the area of the zone sensitive to the weight variation, $L_L$ and $R_L$ represent the contribution of the fluid medium on the coating over the dynamic impedance of the resonator, particularly $L_L$ represents the inertial effect of the equivalent weight of fluid displaced by the oscillating motion of the sensor and $R_L$ represents the corresponding effect of losses; these electrical parameters are also related to the corresponding physical properties by the following expressions: $R_L = \omega K_t m_L$ and $L_L = K_t m_L$, wherein $m_L = \rho_L \delta_L / 2$, is the surface density of the weight equivalent to the liquid in contact with the coating, due to the oscillating motion thereof, wherein $\delta_L = (2\eta_L / \omega \rho_L)^{1/2}$ is the depth penetration of the acoustic wave into the liquid, with $\eta_L$ being the viscosity of the fluid, $\rho_L$ the fluid density and $\omega$ the angular speed of the oscillating motion that matches the electrical signal exiting the resonator. Consequently, the electrical admittance of the resonant sensor, Y, in the described conditions results from the following expression:

$$Y = j\omega C_0^* + \frac{1}{Z_m} \quad (II)$$

wherein $=C_0+C_p$, and $Z_m$ results from:

$$Z_m = R_m + jX_m = R_q + R_L + j\left(\omega(L_q + L_c + L_L) - \frac{1}{\omega C_q}\right) \quad (III)$$

From the previous equation can be obtained the displacement od the dynamic series resonance frequency (DSRF), as defined by the frequency at which the dynamic impedance $Z_m$ has only an actual value, due to a weight variation of the coating; the corresponding angular frequency variation, $\Delta\omega_s$, corresponding to the DSRF is:

$$\Delta\omega_s = -\frac{\omega_s^2}{\pi Z_{cq}} \Delta m_c \quad (IV)$$

wherein $Z_{cq}$ is the characteristic impedance of the material of which the resonator is made, $\omega_s$ is the resonance frequency of the resonator and $\Delta m_c$ is the variation of the weight surface density of the coating.

Equation IV above coincides with the expression for varying the angular resonance frequency, by the effect of a weight variation of the coating, given by Sauerbrey, described in the background and which constitutes the basis of classical methods and systems for characterization processes by microbalance.

The present invention provides a method and an electronic system, different, for the characterization of processes wherein changes occur in the weight of the coating on the resonator. As already mentioned, the invention takes advantage of the deduction of an analytical expression that establishes a simple connection between the phase variation of a fixed frequency signal, which interrogates the piezoelectric resonator, and the variation in the weight density of the coating. This expression shows the connection between the phase variation of a signal with a given frequency, within the resonance region of the loaded sensor, and the weight variation of the coating, is a crucial part of the technique and which has not been demonstrated before.

From the equivalent model shown in FIG. 3, mathematical expressions of which have been included in the equations II and III, it is possible to obtain the displacement of the phase response, at a certain frequency, due to the variation in the weight density of the coating. Indeed, according to the model shown in FIG. 3, changes in the phase-frequency response of the resonator, due to small changes in the weight of the coating, will be the result of the change in the phase-frequency response of the dynamic impedance $Z_m$; in the following deduction there will be assumed that the fluid properties remain substantially constant, i.e. that the dynamic resistance $R_L$ does not significantly change and therefore, the slope of the phase-frequency response of the sensor remains unchanged. This restriction is valid in a wide variety of applications, wherein very small frequency shifts are expected and wherein it is really necessary to increase the sensitivity of the microbalance systems, such is the case of piezoelectric biosensors and many electrochemical applications.

The phase provided by the dynamic branch of the model represented in FIG. 3, in a given reference state, 1, is given by:

$$\varphi_1 = \arctan\frac{X_{m1}}{R_{m1}} \quad (V)$$

wherein $X_m = \omega(L_q + L_c + L_L) - 1/\omega C_q$ and $R_m = R_q + R_L$, with the subindex 1 indicating that are the values corresponding to such state.

About DSRF $X_m$ is small and the tangent can approach to the phase, therefore $\phi_1 \approx X_{m1}/R_{m1}$. After the weight change of the coating, the new phase will be ($\phi_2 \approx X_{m2}/R_{m1}$, since it is assumed that the liquid does not change, and the phase variation from state 1 will result from:

$$\Delta\varphi = \varphi_1 - \varphi_2 = \frac{X_{m1} - X_{m2}}{R_{m1}} \quad (VI)$$

On the other hand, at the frequency of the test signal, $f_t$, $X_m = L_m\omega_t - 1/C_m\omega_t$, wherein $L_m = L_q + L_c + L_L$ and $C_m = C_q$; and the following approximation can be written to $X_m$:

$$X_m = \frac{1}{C_m\omega_t}\left(\frac{\omega_t^2}{\omega_s^2} - 1\right) \approx \frac{2\Delta\omega}{C_m\omega_s^2} \quad (VII)$$

wherein $\Delta\omega = \omega_t - \omega_s$.

Consequently, the phase shift given by equation VI, will be:

$$\Delta\varphi = \frac{2(\Delta\omega_1 - \Delta\omega_2)}{R_{m1}C_m\omega_s^2} = \frac{2\Delta\omega_s}{(R_q + R_L)C_q\omega_s^2} \quad (VIII)$$

wherein $\Delta\omega_s = \omega_{s2} - \omega_{s1}$.

The change in the dynamic series resonance angular frequency due to small changes in the surface weight density of the coating is given by equation IV. Therefore, by using Equation IV in equation VIII, the phase variation between the two states, 1 and 2 is obtained ($\Delta\phi = \phi_1 - \phi_2$):

$$\Delta\varphi(\text{rad}) = -\frac{\Delta m_c}{m_q + m_L} \quad (IX)$$

wherein $m_q = \eta_q\pi/2V_q$, being $v_q = (c_q/\rho_q)^{1/2}$ the propagation speed of the wave in the material of which the resonator is made, where $c_q$ is the modulus of elastic in the vibration mode of the resonator and $\rho_q$ is the density of the material making up the resonator, $\eta_q$ is the equivalent viscosity of the material making up the resonator and which includes friction losses and other due to the contacts with the electrodes and other non-ideal effects. The validity of the previous equation will be confirmed later.

It is important to emphasize that equation IX that relates the phase variation with the weight variation of the coating, will only be valid around the dynamic series resonance frequency; for this reason it is essential to establish a baseline of a initial state, which is taken as reference, using as frequency of the test signal that corresponding to the DSRF of the resonator in such state. This proves that any frequency for the test signal is not valid, but a frequency substantially equal (this term being understood as a frequency equal or close) to the DSRF of the resonator at such reference state. Consequently, it proves being a priority objective of the invention to provide a method that establishes as a frequency of the test signal the DSRF of the resonator in such state of reference and providing a system that allows establishing such frequency using for such purpose a suitable process.

Moreover, the simplicity of equation IX does not preclude highlighting the following key aspects:

- in contrast to the Sauerbrey equation (IV), wherein the frequency shift, associated with the variation in the weight surface density of the coating it does not depend on the fluid medium, equation IX further includes the consideration of the fluid medium. From such equation it is proven that the higher $m_L$ the greater the weight variation of coating will be required to provide a certain shift in the phase. This equation shows the higher sensitivity of the microbalance sensor in gaseous medium than in liquid medium for a given phase stability, due to the reduction of the quality factor of the sensor as a result of contact with the liquid. In other words, Sauerbrey equation predicts the same shift of the resonance frequency for a sensor in vacuum as in liquid, for a certain change in the weight surface density of the coating; however, the corresponding phase shift for the same change in the weight surface density of the coating is lower for the sensor in liquid than in vacuum. Therefore, although Sauerbrey equation ideally the same frequency-weight sensitivity, much more system stability will be needed for the case of the sensor in liquid medium than in vacuum if you want to obtain, in practice, the same sensitivity.
- Furthermore, $m_L$ in equation IX decreases with the reduction of the penetration depth of the acoustic wave in the liquid. This reduction is proportional to $\omega^{1/2}$; therefore the phase-weight sensitivity in a determined fluid medium, for a given phase noise could be improved by increasing the resonance frequency, but only proportional to the square root of the frequency, and not to the square of the resonance frequency as has been assumed in some background of the present invention.
- Even more, the phase-weight sensitivity does not significantly increase with the frequency for the case of sensors in gaseous medium; in particular for the case of vacuum, wherein $m_L$ is zero and wherein the phase-weight sensitivity is the maximum possible for a given piezoelectric material, the phase-weight sensitivity does not increase with the frequency. This aspect has not been considered so far and other inventions mentioned in the state of the art have attempted to use a method based on the phase measurement, to increase the sensitivity in the measurement of the weight variation, increasing the resonance frequency of the sensor, when this increase of the phase-weight sensitivity is not significant in gaseous medium. Accordingly, increasing the resonance frequency for increasing the phase-weight sensitivity has sense in liquid media and yet the increase in the sensitivity is only proportional to the square root of the resonance frequency; therefore it is interesting to keep the possibility of monitoring the resonance frequency as well as the measurement of the phase shift thereof. This proves to be a non-trivial object of the invention to provide a system that allows measuring the phase change and, additionally, the resonance frequency change.

These key aspects are then brought to light from a non-limiting example applying equation IX to the case of resonators based on AT quartz crystals of different resonant frequencies. The physical properties of the AT-cut quartz crystal are shown in table I.

TABLE I

Properties of AT Quartz

| Parameter | Value | Description |
|---|---|---|
| $e_{26}$ (A s m$^{-2}$) | 9.657E−02 | Piezoelectric constant |
| $\epsilon_{22}$ (A$^2$s$^4$Kg$^{-1}$m$^{-3}$) | 3.982E−11 | Permittivity |
| $C_{66}$ (N m$^{-2}$) | 2.947E+10 | Elastic constant |
| $\rho_q$ (Kg m$^{-2}$) | 2651 | Density |
| $V_q = (C_{66}/\rho_q)^{1/2}$ (m s$^{-2}$) | 3334.15 | Wave propagation speed |
| $K_o^2$ | 7.947E−03 | Electromechanical coupling factor |
| $Z_{cq}$ (Kg m$^{-2}$ s$^{-1}$) | 8.839E+06 | AT quartz characteristic impedance |
| $\eta_q$(*) (Pa s) | 9.27E−03 | AT quartz effective viscosity |
| $m_q = \eta_q \pi/2v_q$ (ng/mm$^{-2}$) | 4.37 | $M_q$ in Equation IX |

(*)It is an effective viscosity obtained for AT quartz crystals of 10 MHz in air, from the experimental values of $R_q$ and $C_q$ obtained with an impedance analyzer.

Table II shows the detection capability according to equation IX with AT quartz crystal microbalance sensors for different resonance frequencies, and in contact with different media for a phase detection limit of 0.1°; the corresponding frequency shift according to Sauerbrey equation is also included for comparison. As can be seen the same phase-weight sensitivity is obtained in vacuum for all sensors because the same value of $\eta_q$ (see Table I) has been used; consequently the same value of $\Delta m_c$ is needed to achieve the same lag of $\Delta\phi$=0.1°. Therefore, in order to increase the sensitivity in vacuum is necessary to increase the wave propagation speed using another material for the resonator, or reducing the sources of losses.

TABLE II

Weight sensitivity for phase detection limit of 0.1°

| Media | $\rho_L$ (Kg/m$^3$) | $\eta_L$ (Pa s) | $f_s$ (MHz) | 10 | 50 | 150 |
|---|---|---|---|---|---|---|
| Vacuum | 0 | 0 | $\Delta m_C$ | 7.62 | 7.62 | 7.62 |
| Hydrogen | 0.08988 | 8.6 10$^{-6}$ | (pg/ | 7.76 | 7.68 | 7.66 |
| Air | 1.18 | 1.783 10$^{-5}$ | mm$^2$) | 8.34 | 7.94 | 7.81 |
| Water | 1000 | 0.001 | | 163.32 | 77.25 | 47.82 |
| Vacuum | | | $\Delta f_s$ | 0.17 | 4.31 | 38.81 |
| Hydrogen | | | (Hz) | 0.18 | 4.35 | 38.99 |
| Air | | | | 0.19 | 4.49 | 39.75 |
| Water | | | | 3.70 | 43.70 | 243.47 |

It also shows that the phase-weight sensitivity for gaseous media does not significantly increase when increasing the frequency, as announced; this aspect shows the error of previous inventions by assuming that the phase-weight sensitivity would increase in the same way as that of frequency-weight by increasing the frequency of the resonator.

However, the scope of the present invention, wherein the media where the experiments are developed is a liquid media, an increase of the phase-weight sensitivity is obtained by increasing the resonance frequency of the sensor, due to the reduction of the penetration depth and, therefore, at the lower equivalent weight of fluid that moves the resonator when vibrating. As can be seen a large increase in the frequency shift occurs as Sauerbrey predicts, however, it is necessary to point out that this frequency shift corresponds to the same phase shift of 0.1°, therefore, although the frequency-weight sensitivity has increased about 225 times between the sensor of 150 MHz and of 10 MHz, which corresponds to the squared frequency ratio, the phase-weight sensitivity has increased only 3.4 times, which approximately corresponds to the square root of the frequencies ratio, i.e. inversely proportional to the relative decrease of the penetration depth of the fluid wave.

Modern phase detectors can detect phase shifts below 0.1° even at very high frequencies; therefore, if the phase stability of the system is not reduced below 0.1°, the real improvement in the sensitivity will be 3.4 times and not 225 times, since the sensitivity of frequency depends on the phase noise of the system. Thus, the most important aspect to increase the weight sensitivity, is to improve the phase stability of the system for characterization and, at the same time, performing a system that is capable of detecting very small phase shifts in the response of the sensor; otherwise, it will be irrelevant to increase the frequency-phase sensitivity using higher resonance frequency resonators, since the frequency noise in oscillators, due to the phase instability of the oscillating system, it would be of same magnitude as the frequency shift associated to the weight variation intended to be detected, making impracticable the improvement of the sensitivity.

Assuming that the configuration of the experimental measurement system has been designed in the best suited shape to reduce disturbances on the sensor, the remaining priority objective is to provide an electronic system for characterization wherein the frequency and phase noises are minimal.

Thus, there is clear that another priority and non-trivial object of the present invention is to provide an electronic system for characterizing the phase shift of a resonant sensor wherein phase and frequency noises are minimal.

Moreover, it is a fundamental objective of the system embodiment to provide a measure of the lag as close as possible to the lag produced by the dynamic impedance of the sensor, wherein equation IX is valid.

It is another object of the invention that the characterization system allows implementing a procedure to establish the frequency of the test signal substantially equal (this term being understood as a frequency equal or close) to the dynamic series resonance frequency of the sensor in the state considered as a reference, since equation IX is only valid around such frequency.

It is still another important object of the invention to provide a system for determining whether the characteristics of the fluid medium change during the experiment, for ensuring the validity of the results obtained when applying equation IX. A system of such characteristics will allow applying the method of the invention operations of which have been previously described.

Figure 4:
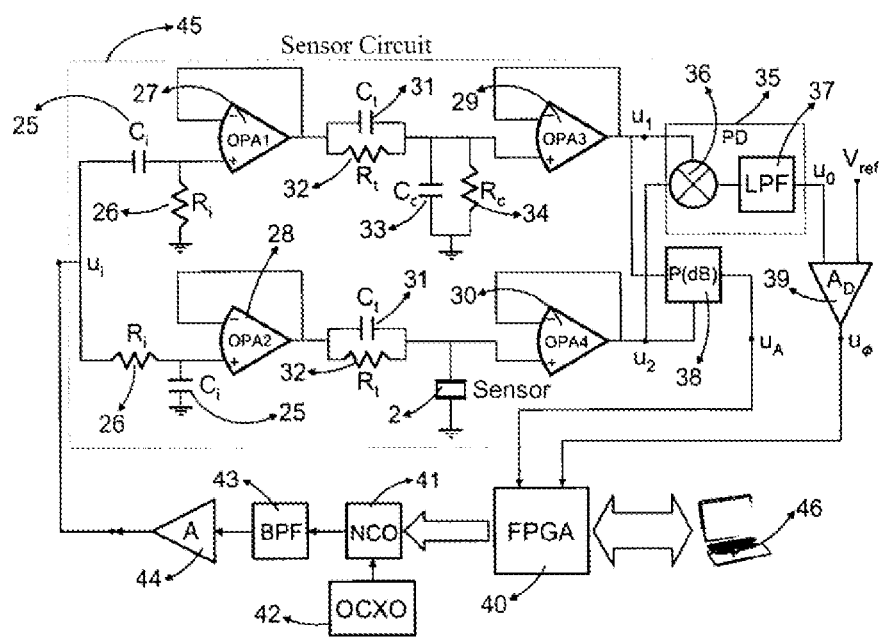
FIG. 4.—Schematically represents a circuit, object of the invention, for monitoring the phase variation in a fixed frequency signal due to the change in the phase-frequency response of the piezoelectric sensor in its path.

FIG. 4 shows a preferred embodiment of the electronic characterization system for microbalance sensors object of the invention, which consists of:
- a source of certain fixed frequency, with high stability and low phase noise signal 42,
- a frequency synthesis subsystem 41;
- a signal control and acquisition subsystem 40;
- a signal conditioning circuit with filtering capability and adequacy of power levels formed by the filter 43, and the amplifier 44;
- a circuit 45 formed by two branches that share the input $u_i$ and has two outputs, $u_1$ and $u_2$, one for each branch. One branch is composed of components 25, 26, 27, 29, 31, 32, 33, 34, phase-frequency response of which does not change; the other one includes, in part, the same components as the first 25, 26, 28, 30, 31, 32, as a mirror, but a part of the components is replaced by the resonant sensor 2;
- an adjustable gain phase detection subsystem 35, formed by the multiplier 36 and the low pass filter 37, which provides a voltage signal $u_0$ proportional to the phase difference between the signals at their inputs;
- a power measurement subsystem 38 that provides a voltage signal $u_4$ proportional to the difference between power levels of signals at their inputs; and
- an external processing element 46;

and characterized in that:
- the frequency synthesis subsystem 41 provides, from the fixed frequency signal of the source 42, a signal frequency of which can sweep the band of resonance frequencies of the resonator sensor 2;
- the signal provided by frequency synthesis subsystem 41 is connected to the input of the filter 43, which adequately filters it and output of which is connected to the amplifier 44 that provides the appropriate power level;
- the output $u_i$ of the amplifier 44 is connected to the input of the circuit of two branches 45 wherein the resonant sensor 2 is connected;
- each of the outputs of the circuit of two branches $u_1$ and $u_2$, is connected to one input of the phase detection subsystem 35, output of which provides a continuous voltage signal $u_0$ with a value proportional to the phase difference between the signals $u_1$ and $u_2$ at their inputs;
- each one of the outputs $u_1$ and $u_2$ of the two branches circuit is also connected to one input of the power measurement circuit 38, output of which provides a continuous voltage signal $u_4$ with a value proportional to the power levels difference between the signals at their inputs;
- the outputs of the phase detection circuitry and of the power level are acquired by the control system 40 that can act on the frequency synthesis subsystem 41 to control the frequency of the output signal from said subsystem;
- the data from the signals acquired by the control system are directly analyzed, or either transferred to an external equipment 46 for processing thereof in real time or later in accordance to the method object of the present invention.

As mentioned above, it is a priority objective that the system provides a signal proportional to the phase variation that occurs in dynamic impedance of the sensor, this aspect is not trivial since the system in turn disturbs the phase measurement. It will be shown below that by using a suitable selection of the components of the presented system it is possible to achieve this goal.

Firstly, the measurement of the lag between the signals $u_1$ and $u_2$ is obtained from the phase detector 35, in effect, assuming that the signals $u_1$ and $u_2$ are peak amplitude sine, $U_1$ and $U_2$, respectively, angular frequency $\omega$ and with a phase shift a certain amount $90° - \phi_D$, the output of the multiplier 36 will be:

$$u_1 \cdot u_2 = U_1 \sin\omega t \cdot U_2 \sin(\omega t + 90° - \phi_D) = \qquad (X)$$

$$= \frac{U_1 U_2}{2}[\sin(\phi_D) - \cos(2\omega t - \phi_D + 90°)]$$

Therefore, the output of the low pass filter $u_0$, will be:

wherein $k_m = U_1 U_2 / 2$

As shown, the behavior of the phase detector based on multiplier provides a voltage tension proportional to the time lag between the signals at their inputs for small laps around 90°. Therefore, for a proper functioning of the phase detector is necessary to previously offset 90° the test signals in each branch of the sensor circuit 45; for this purpose the circuits formed by resistors 26 and capacitors 25, have been arranged in both branches. These offset networks must be properly designed to obtain lag signals 90° and with an amplitude similar to their outputs. This requirement that is necessary by using a multiplier as a phase detector could be avoided by using other types of phase detectors based on digital circuits, however the phase noise of these circuits are not suitable for the object of the invention since these would increase the phase noise. Moreover, the differential system raised from the sensor circuit 45, is very convenient since the original phase noise in the input signal $u_i$, is equally transmitted to both branches and can be canceled at least partially, in the phase detector 35.

The output of the phase detector 35 is connected to the input of an amplifier 39. The reference voltage $V_{ref}$ is used to set the output voltage of the amplifier 39 to zero volts in the reference state, compensating for any shift of continuous voltage; this allows increasing the gain of the amplifier 39 for providing the maximum resolution in monitoring the lag, which will be provided by the output signal $u_\phi$ of the amplifier 39.

The output signals from the sensor circuit 45 are also connected to a power measurement circuit 38, which provides an output signal $u_A$ proportional to the ratio between the signal powers at their inputs. This combination of phase and power measurement provides a complete characterization of the sensor and allows selecting the appropriate test frequency by using an appropriate control system. The control system 40 includes an embedded programmable system that continually monitors the lag and the ratio of powers between the signals $u_1$ and $u_2$ from the signals $u_\phi$ and $u_A$, the programmable system 40 controls the frequency synthesizer 41, and thus the frequency of the output signal of the same. The frequency synthesizer uses as a reference signal that provided by a source of high frequency stability and phase 42. The output signal of the synthesizer is connected to a band-pass filter 43 which filters it providing at its output a signal sufficiently pure in the resonance frequency band of the sensor. The output of the filter 43 is connected to the input of the amplifier 44 which provides a signal at its output $u_i$ with adequate power.

The variation of the lag between the signals $u_1$ and $u_2$ is the main parameter, which must be related to the phase shift experienced by the dynamic branch of the resonant sensor. This connection will be obtained below in relation to the system shown in FIG. 4.

After a basic analysis, the connection between the signals $u_1$ and $u_2$ and the input signal $u_i$, are given by the following expressions:

$$u_1 = \frac{R_c(1+j\omega R_t C_t)}{R_t + R_c + j\omega R_t R_c (C_t + C_c)} \frac{j\omega R_i C_i}{1+j\omega R_i C_i} u_i \quad \text{(XII)}$$

$$u_2 = \frac{(R_m + jX_m)(1+j\omega R_t C_t)}{R_t + R_m - \omega R_t(C_t + C_0)X_m + j[X_m + \omega R_t R_m(C_t + C_0)]} \frac{1}{1+j\omega R_i C_i} u_i \quad \text{(XIII)}$$

In obtaining the above expressions it is assumed that the operational amplifiers 27, 28, 29 and 30 operate as ideal followers.

From equations XII and XIII it is possible to obtain the expression of the lag variation between the signals $u_1$ and $u_2$. Indeed, the phase of the signals $u_1$ and $u_2$ relative to $u_i$, will be $$\phi_1 = \phi_{Zt} - \phi_{Zct} + 90° - \phi_{Zi} \quad \text{(XIVa)}$$

$$\phi_2 = \phi_{Zm} + \phi_{Zt} - \phi_{Zmt} - \phi_{Zi} \quad \text{(XIVb)}$$

wherein
$\phi_{Zt}$=a tan $\omega_t R_t C_t$, $\phi_{Zct}$=a tan $\omega_t R_t R_c(C_t + C_c)/(R_t + R_c)$, $\phi_{Zi}$=a tan $\omega_t R_i C_i$,
$\phi_{Zm}$=a tan $X_m/R_m$, y $\phi_{Zmt}$=a tan $[X_m + \omega_t R_t R_m(C_t + C_0)]/[R_t + R_m) - \omega_t R_t(C_t + C_0)X_m]$.

Therefore, the lag between $u_1$ and $u_2$ will result from:

$$\phi_2 - \phi_1 = \phi_{Zm} - \phi_{Zmt} + \phi_{Zct} - 90° \quad \text{(XV)}$$

Consequently, the variation between the lag in a reference state "1" and a second state "2", taking into account that the test frequency $f_t$ is constant, will be:

$$\Delta(\phi_2 - \phi_1)|_1^2 = \Delta(\phi_{Zm} - \phi_{Zmt})|_1^2 \quad \text{(XVI)}$$

After some approximations and calculations, the following expression is obtained from equation XVI:

$$\Delta(\varphi_2 - \varphi_1)\Big|_1^2 \approx \Delta\varphi \frac{R_t}{R_t + R_m} \quad \text{(XVII)}$$

wherein $\Delta\phi$ is the phase variation of the dynamic impedance given by equation IX. Consequently equation XVII becomes:

$$\Delta(\varphi_2 - \varphi_1)\Big|_1^2 \approx \frac{\Delta m_c}{m_q + m_L} \frac{R_t}{R_t + R_m} \quad \text{(XVIII)}$$

As can be seen from equation XVIII, for a value of $R_t \gg R_m$ the second term on the second member the equation tends to 1 and the lag variation given in XVIII tends to that of the dynamic impedance given by IX. For practical reasons, in order not to reduce too much the amplitude of the signals at the input of phase detector, is sufficient to choose $R_t = 10 R_m$.

Since the test frequency is held constant, the network formed by $R_c$ and $C_c$ does not contribute to the lag variation, however it is advisable to select $R_c$ and $C_c$ of a value similar to $R_m$ and $C_0$ respectively. Indeed, under these conditions, and the DSRF of the sensor, the signal level at the output of those operational 29 and 30 is similar, which it is desirable for optimal operation of the phase detector, and the voltage output of the power meter 38 is zero. This configuration is also useful to select the frequency of the test signal in the reference state "1" as the tensions $u_\phi$ and $u_A$ are zero at such frequency.

Figure 5:
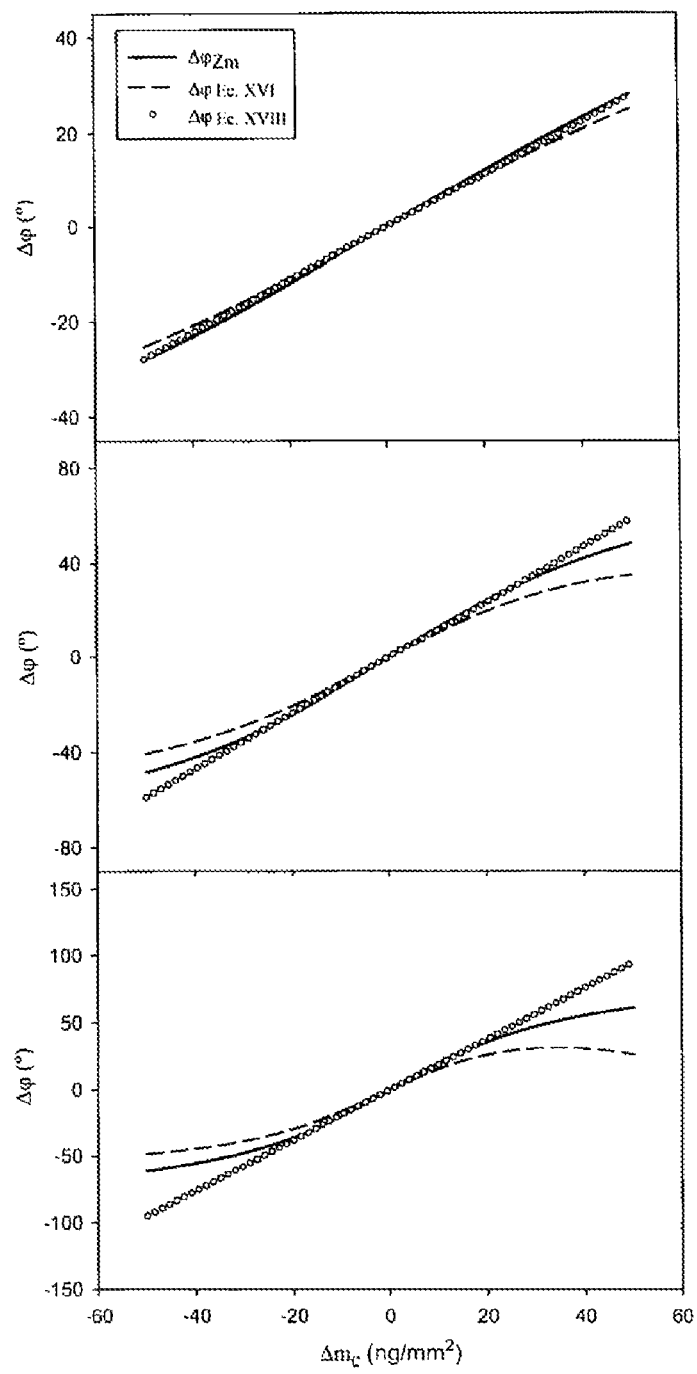
FIG. 5.—It is a graph showing a comparison of the results obtained for the phase variation of the dynamic impedance and equations XVI and XVIII, which are deducted in the following detailed description, for three AT quartz sensors of different resonance frequencies, around the dynamic series resonance frequency of each one.

FIG. 5 shows a comparison between the values of lag variation obtained for the dynamic impedance, and those provided by equation XVI and equation XVIII. Equation XVI is an expression that provides the exact phase variation between the signals $u_1$ and $u_2$, whereas equation XVIII is a simplified expression that approximates equation IX when $R_t$ is much higher than $R_m$ (in the case of figure we have chosen $R_t = 10 R_m$). The results presented in FIG. 5 are obtained from a non-limiting example and demonstrate validity of the expression IX as an approximation of the lag variation associated with the dynamic impedance, and the expression XVIII as an approximation to equation XVI.

The results shown in FIG. 5 were obtained from numerical simulations using the circuit shown in FIG. 3 as an equivalent model of the behavior of resonant sensor in contact by one side with a fine acoustic coating that is in contact with a Newtonian fluid media; this is the case of the majority of applications for characterizing biological processes, such as piezoelectric biosensors and many electrochemical applications falling within the scope of the present invention.

Numerical simulations have been performed for three AT cut quartz crystal resonant sensors and with resonance frequencies of 10, 50 and 150 MHz, in contact with a thin layer having a thickness of 100 nm and a density equal to that of the water; the Newtonian fluid was considered with the same properties as water. Equivalent model parameters were calculated according to the terms provided in the following reference: R. Lucklum, D. Soares and K. K. Kanazawa, "Models for resonant sensors," in *Piezoelectric Transducers and Applications,* 2nd Ed., pp 63, A. Arnau Ed., Springer-Verlag Berlin Heidelberg, (2008), with the AT quartz properties given in Table I, departing from the frequency of the resonator and the typical diameter of the electrode for commercially available sensors: for sensors of 10 MHz 5.2 mm, and 50 y 150 MHz 1.5 mm. The quartz effective viscosity was obtained from experimental data with the sensors of 10 MHz in air and the value of the dynamic resistance $R_Q$ obtained with an impedance analyzer, which was approximately 10Ω. The thicknesses of the resonators were calculated from the expression $h_q \approx V_q/2f_s$. The remaining parameters of the model and other amounts are included in Table III.

calculated; as can be seen by simple inspecting equations XII and XIII, the capacitor $C_t$ may be void without any restriction, therefore $\phi_{Zt}=0$, which improves the functioning at high frequencies.

Finally, the simulation of the lag variation was assessed by taking as reference the state of the sensor for $\Delta m_c=0$. The results from the lag in the dynamic impedance, and those provided by equations XVI and XVIII in this simulation are shown in FIG. 5 for sensors of 10 MHz (upper panel), 50 MHz (middle panel) and 150 MHz (lower panel). These results demonstrate the validity of equation IX providing a simple approximate expression for the lag of the dynamic impedance and of the expression XVIII and the proposed system to measure such lag and its variation.

Figure 6:
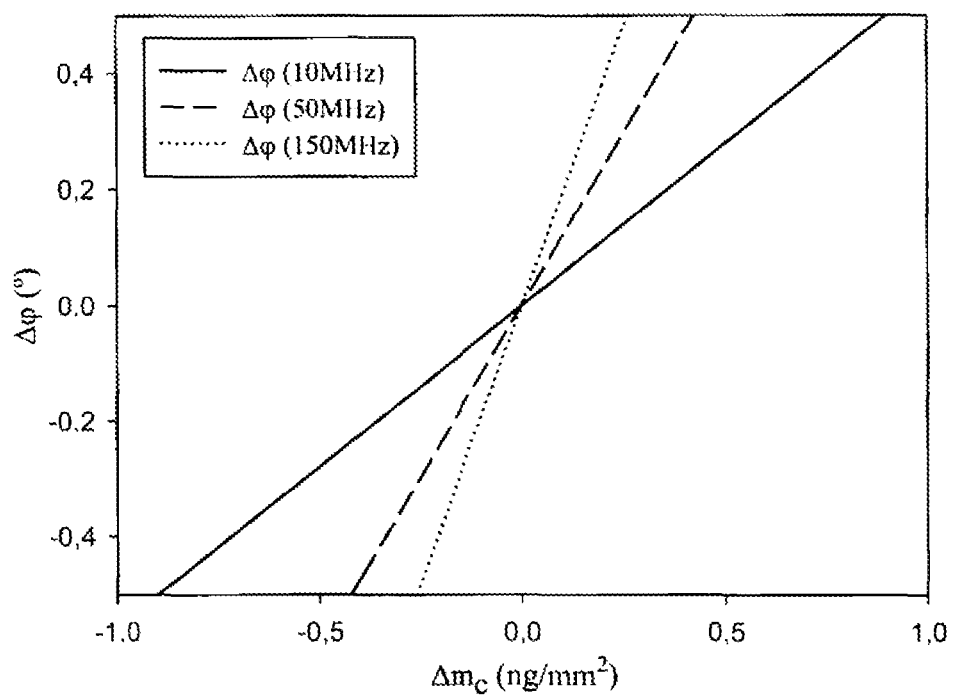
FIG. 6.—It is a graph showing a comparison of the phase-weight sensitivities of three sensors of different resonance frequencies.

FIG. 6 is a local expansion, extracted from each of the panels of FIG. 5, which shows a comparison of the sensitivities of the three microbalance sensors (10, 50 and 150 MHz) in terms of phase variation in function of the weight variation.

TABLE III

Properties and parameters of the model shown in FIG. 3 for three AT-quartz sensors of different resonant frequencies and loaded with a thin weight layer of 100 nm thick and a density equal to that of water, in contact with liquid with properties, such as water.

| Parameter | Sensor 1 | Sensor 2 | Sensor 3 | Description |
|---|---|---|---|---|
| $f_{s0}$ (Hz) | 10000000 | 50000000 | 150000000 | RSD Frequency |
| $h_q$ (m) | 1.66E−04 | 3.334E−05 | 1.111E−05 | Quartz thick |
| $d_e$ (m) | 5.20E−03 | 1.50E−03 | 1.50E−03 | Electrode diameter |
| $A_e$ (m$^2$) | 2.12E−05 | 1.77E−06 | 1.77E−06 | Electrode area |
| $C_o$ (pF) | 5.07 | 2.11 | 6.33 | Static capacitance |
| $C_p$ (pF) | 2.00 | 2.00 | 2.00 | Parallel parasitic capacitance |
| $C_o*$ (pF) | 7.07 | 4.11 | 8.33 | Total parallel capacitance |
| $C_q$ (fF) | 32.7 | 13.6 | 40.8 | Dynamic capacitance |
| $L_q$ (µH) | 7751.8 | 745.28 | 27.603 | Dynamic inductance in vacuum |
| α | 3.1416 | 3.1416 | 3.1416 | Acoustic wave phase |
| $K_t$ (Ωm$^2$skg$^{-1}$) | 3.51E−02 | 1.69E−02 | 1.87E−03 | Electroacoustic constant |
| $\eta_q$ (Pa s) | 9.27E−03 | 9.27E−03 | 9.27E−03 | Quartz effective viscosity |
| $R_q$ (Ω) | 9.63 | 23.14 | 7.71 | Dynamic resistance in vacuum |
| Parameters associated with the load | | | | |
| $m_c$ (ng/mm$^2$) | 100 | 100 | 100 | Weight density of the coating |
| $L_c$ (µH) | 3.51 | 1.69 | 0.187 | Coating inductance |
| $\delta_L$ (nm) | 178.4 | 79.79 | 46.07 | Penetration depth |
| $m_L$ (ng/mm$^2$) | 89.21 | 39.89 | 23.03 | Equivalent weight density of the liquid |
| $L_L$ (nH) | 3129 | 672.8 | 43.16 | Inductance associated with liquid |
| $L_m$ (µH) | 7758.5 | 747.64 | 27.833 | Total inductance |
| $R_L$ (Ω) | 196.63 | 211.36 | 40.68 | Water dynamic resistance |
| $R_m$ (Ω) | 206.25 | 234.49 | 48.39 | Total dynamic resistance |
| $C_m$ (fF) | 32.7 | 13.6 | 40.8 | Total dynamic capacitance |
| $f_{sL}^o$ (Hz) | 9995721.5 | 49921051.2 | 149377514.8 | DSRF in load |

Under these conditions the weight variation of the coating was simulated by changing the thickness thereof in steps 1 Å, i.e. in steps of 100 pg/mm$^2$, from −50 nm/mm$^2$ to 50 nm/mm$^2$. For each step the phases $\phi_{Zm}$ and $\phi_{Zmt}$ in equation XVI were An important consideration is that the system object of the invention can be used to monitor the DSRF of the sensor during the experimental process. Indeed, since the lag and the ratio of power is continuously measured by the system, the frequency of excitation can be changed so that the voltages $u_\varphi$ and $U_A$ are continuously maintained to zero, thus making a continuous monitoring of the DSRF. This continuous monitoring of the DSRF can also be performed by a correction in the frequency of the test signal according to a specific function, for example an integral or quasi-integral variation of the variations that occur in the voltage signal that provides the phase variation of the sensor.

Another aspect that is important to emphasize, is that eventually the frequency of the test signal can be located, upon the change in the response of the sensor as a result of the weight variation, in a low or zero phase-weight sensitive area. The method object of the invention in conjunction with the system object of the invention provides a method for determining this eventuality and correcting the properly frequency of the test signal.

It is also important to highlight that can be used two or more systems like those described, one of which includes a reference sensor, uncoated, in contact with the liquid media, in a differential configuration to minimize the external effects that can disrupt the measurement, such as changes in the temperature, environmental, etc.; this provides a system that allows the cancellation of the external effects of the sensor, as was another of the objects of the invention.

The invention has been generally described in detail and has also been described in connection with one of its possible embodiments. Obviously, there may be modifications on this embodiment intended to be included in the invention. Having thus described an embodiment chosen for our invention, we claim that this is:

The invention claimed is:

1. A method for determining a mass surface density change of a coating deposited on a piezoelectric resonator exposed to a fluid medium, the resonator acting as a sensor connected to a circuit to which a test signal is applied, and the fluid medium being such that physical characteristics remain stable during an experimental process, the method comprising:
   a) selecting the frequency of a test signal substantially equal to the dynamic series resonant frequency of the resonator in an initial state of the resonator, taking such state as a reference;
   b) measuring the values of two voltage signals, one of which establishes the phase reference of the sensor and the other one establishes the reference of the loss level thereof;
   c) monitoring the voltage values taken as a reference in said measuring operation during the experimental process that is to be monitored;
   d) verifying that the value of the loss reference voltage of the sensor does not essentially change during the measurement process;
   e) correcting the value of the frequency of the test signal during the experimental process to be monitored, in the event that the signal provided by the measurement of the phase variation has been deviated above or below a predetermined value based on the features of the experiment, the voltage value obtained as a phase reference of the sensor in said step b), until the voltage signal that provides the measurement of the phase variation again has the same value as that obtained by phase reference of the sensor in said step b), or its difference in absolute value is less than a certain predetermined number depending on the characteristics of the experiment; and
   f) obtaining the mass surface density change on the coating during the experimental process from the variations of the voltage signal that provides the measurement of the phase variation by calculating the mass surface density change as a function of the phase variation of the voltage signal that provides the measurement of the phase variation.

2. The method of claim 1, wherein said obtaining the mass surface density change on the coating is performed by applying the following expression:

$$\Delta\varphi(\text{rad}) = -\frac{\Delta m_c}{m_q + m_L}.$$

3. The method of claim 1, wherein said step e) is continuously performed by providing a correction to the frequency of the test signal according to an integral or quasi-integral variation of the variations that occur in the voltage signal that provides the phase variation of the sensor.

4. The method of claim 1, wherein the piezoelectric resonator is a thin film acoustic resonator.

5. The method of claim 1, wherein the piezoelectric resonator is a resonator vibrating in shear mode.

6. The method of claim 1, wherein said obtaining the mass surface density change indicates the concentration of a certain material or chemical or biological compound in the liquid solution that is contact with the coating.

7. The method of claim 1, applied to simultaneously interrogate several piezoelectric sensors.

8. The method of claim 1, further comprising providing a device for determining mass surface density change of a coating deposited on a piezoelectric resonator exposed to a fluid medium, the resonator acting as a sensor connected to a circuit to which a test signal is applied, and the fluid medium being such that physical characteristics remain stable during an experimental process, the device comprising:
   a piezoelectric resonator integrated as a resonant sensor on a surface of which a material shaped as a thin layer has been physically or chemically deposited;
   a signal source of determined frequency;
   a frequency synthesis subsystem;
   a signal control and acquisition subsystem;
   a signal conditioning circuit with filtering capability and adequacy of power levels, the signal conditioning circuit having a filter and an amplifier;
   a circuit formed by two branches that share an input ($u_i$) and which has two outputs, ($u_1$ and $u_2$), one for each branch, with one branch being composed of components, phase-frequency response of which does not change, and the other branch includes the same components as the first branch, as a mirror, and the resonant sensor;
   an adjustable gain phase detection subsystem, formed by a multiplier and a low pass filter, which provides a voltage signal ($u_0$) proportional to the phase difference between the signals at their inputs ($u_1$, $u_2$); and
   a power measurement subsystem that provides a voltage signal ($u_A$) proportional to the difference between power levels of signals at their inputs ($u_1$, $u_2$),
   wherein the frequency synthesis subsystem provides, from the determined frequency signal of the source, a signal frequency of which can sweep the band of resonance frequencies band of the resonator sensor,
   wherein the signal provided by frequency synthesis subsystem is connected to the input of the signal conditioning circuit, formed by the filter and the amplifier, which adequately filters it and provides the appropriate power level, wherein the output ($u_i$) of the amplifier is connected to the input of the circuit of two branches wherein the resonant sensor is connected, wherein each one of the outputs ($u_1$, $u_2$) of the circuit of two branches, is connected to one input of the phase detection subsystem, output of which provides a continuous voltage signal ($u_O$) with a value proportional to the phase difference between the signals ($u_1$, $u_2$) at their inputs, wherein each one of the outputs ($u_1$, $u_2$) of the two branches circuit is also connected to one input of the power measurement circuit, output of which provides a continuous voltage signal ($u_A$) with a value proportional to the power levels difference between the signals ($u_1$, $u_2$) at their inputs, wherein the outputs of the phase detection circuitry and of the power level are acquired by the control system that can act on the frequency synthesis subsystem to control the frequency of the output signal from said subsystem.

9. The method of claim 8, further comprising simultaneously interrogating several piezoelectric sensors.

10. A device for determining a mass surface density change of a coating deposited on a piezoelectric resonator exposed to a fluid medium, the resonator acting as a sensor connected to a circuit to which a test signal is applied, the device allowing conducting flowing experiments on piezoelectric resonators, and the fluid medium being such that physical characteristics remain stable during an experimental process, the device comprising:

a support part on which a resonant sensor is deposited;

a lower block on which is deposited the support part, the lower block being configured for connecting the electrodes of the resonant sensor to an external connector;

an upper block deposited on the support part, the upper block including a set of channels and fittings for channeling flow of the fluid medium;

wherein the support part has a hole which fixes a position of the support part on the lower block, and the support part has a lower face which includes (i) a central hole wherein the resonant sensor is deposited, and which is a through hole configured to leave accessible the central area of one of the electrodes of the resonator by the upper circular face of the support part, (ii) slots starting from the central hole and extending toward outer edges of the support part without reaching the outer edges, (iii) ribs that act as walls between the slots and the central gap, and (iv) another rib that borders the central hole of the gap, leaving at the same height as the other ribs, so that when the resonant sensor is introduced into in the gap, this is deposited on the ribs, wherein the ends of the electrodes of the resonant sensor reach the slots over the ribs, wherein a sealing material fills the gap between the lower surface of the resonant sensor and the ribs;

wherein a conductive material is deposited along the length and width of the slots and to the extent of the ribs which are separating the slots of the central gap, the conductive material establishing electrical contact with the ends of the electrodes of the resonant sensor, wherein the lower block includes (i) a gap in which the support part and, above said support part, the upper block is deposited, (ii) two holes on the bottom of the previous gap into each of which there are introduced two contact elements, upper ends of the contact elements being in contact with the conductive material deposited on the slots of the support part and yielding when a pressure is made thereon, and lower ends of which are configured to be connected to an external bipolar connector, wherein the upper block is deposited on the support part and embedded in the gap of the lower block, and the gap is configured to serve as guide during a placement process on said support part, wherein a washer is seated on a slot in an underside of the upper block and said washer presses on the support part, surrounding the central hole of the support part through which is accessible the central area of one of the electrodes of the resonant sensor, and wherein two tubular channels start from fittings located in the upper part of the upper block and leading in the lower central part, within the lower central area to the washer.

* * * * *